United States Patent [19]

Halpern et al.

[11] 3,989,033

[45] Nov. 2, 1976

[54] SURGICAL INSTRUMENT FOR BIOPSIES

[76] Inventors: David Marcos Halpern, Fragata Presidente Sarmiento 797; Eduardo Raúl Sánchez; Arnoldo Livoff, both of Avda. Cordoba 679, all of Buenos Aires, Argentina

[22] Filed: Dec. 5, 1974

[21] Appl. No.: 529,928

[30] Foreign Application Priority Data

Dec. 6, 1973  Argentina ........................ 251399

[52] U.S. Cl. ............................... 128/2 B; 128/305
[51] Int. Cl.[2] ......................................... A61B 10/00
[58] Field of Search ............ 128/2 B, 305, 310, 347, 128/329

[56] References Cited

UNITED STATES PATENTS

| | | | |
|---|---|---|---|
| 2,710,000 | 6/1955 | Cromer et al. | 128/2 B |
| 3,001,522 | 9/1961 | Silverman | 128/2 B |
| 3,404,677 | 10/1968 | Springer | 128/2 B |
| 3,561,429 | 2/1971 | Jewett et al. | 128/2 B |
| 3,835,860 | 9/1974 | Garretson | 128/310 |
| 3,870,048 | 3/1975 | Yoon | 128/2 B X |

FOREIGN PATENTS OR APPLICATIONS

| | | | |
|---|---|---|---|
| 1,160,573 | 1/1964 | Germany | 128/2 B |
| 146,433 | 8/1962 | U.S.S.R. | 128/2 B |

*Primary Examiner*—Kyle L. Howell

[57] ABSTRACT

A surgical instrument is disclosed for extracting specimens from an organ which comprises particularly configured cutting elements. In particular, the elements are so configured and arranged that they penetrate the organ by means of a substantially cylindrical incision and, immediately thereafter, perform a finishing cut which separates from the organ the cylindrical specimen corresponding to the incision.

In one embodiment of the invention, the cutting elements employed are a punch and rotating guillotine or knife. In a second embodiment, the guillotine is replaced by a cutting element comprising two faced clamps, each being in the form of a chute, trough or convex member having a sharpened point and sharpened longitudinal edges.

8 Claims, 7 Drawing Figures

SURGICAL INSTRUMENT FOR BIOPSIES

BACKGROUND OF THE INVENTION

1. Field of the Invention

This invention relates to a surgical instrument for biopsy purposes and, in particular, to a device for medical use in the extraction of specimens destined to be employed for histological examinations of diseased organs or other parts of the body.

2. Description of the Prior Art

More specifically, the present invention covers a surgical instrument which, by means of a procedure carried out in a few minutes, can be used to extract specimens from internal body areas, particularly from the stroma, epithelial tissue, etc., which are commonly surrounded by mucous substances. Usually, due to the mucous nature of these areas, difficulties and complications arise when the instruments in use today are employed.

In particular, to extract such specimens well-known instruments such as Schubert's coude clamps or Hartman's and Faure's extractors have been utilized. Due to the presence of the mucous substances already mentioned, such instruments are difficult to manage and often the specialist using them cannot insert them into the exact region where the extraction is to be made. Moreover, these prior art instruments often disintegrate the portions to be analyzed, and many times the pieces extracted are not significant enough to be able to be used for biopsy purposes. As a result, in many instances, the procedure must be repeated, causing strain and discomfort for the patient.

All the above-mentioned problems encountered with prior art devices are substantially eliminated when employing the surgical device of the present invention. It is capable of extracting full, clean-cut cylindrical pieces in a very short time that is practically instantaneous. The device has the further advantage of affording easy manageability in the presence of mucous substances, thereby permitting the physician to insert the device in the desired region easily and without the confusion ordinarily encountered using prior art instruments.

SUMMARY OF THE INVENTION

The above and other advantages are a direct consequence of the special combination of functions performed by the surgical instrument of the present invention. In particularly, the present surgical device functions to penetrate the affected organ by means of an incision substantially cylindrical, and, further, it functions to complement such penetrating action by a substantially simultaneously occurring finishing cut which separates from the organ a cylindrical piece corresponding to the incision.

The separation of the cylindrical piece, which constitutes the specimen adequate for subsequent analysis, is done practically simultaneously by a combination of the stretching effects of such piece, or by a cut at the bottom of the incision, complemented by another cut so that the piece is totally housed at the end of the instrument and separated from the affected organ. In this way, when the device is pulled out, the specimen is retained at its end, and, thus, can be easily retrieved once the operative stage is ended with respect to the patient.

The surgical device of the present invention can take on a number of embodiments. These embodiments differ in detail with respect to the functioning of some of their parts, but, in their concept, they conform to the present inventive purpose, which is, to obtain a cylindrical incision, to cut the portion included in such incision and, finally, to extract the piece cut in this way.

In a first embodiment of the invention, the incision is made by a cutting element or member similar to a punch. After an air-suction stretching of the same is accomplished, a cut of the cylindrical portion determined by the punch is made. Another cutting element makes the cut, the latter element being in the guise of a rotary guillotine or knife which cross sections the above-indicated stretched portion.

In a second embodiment of the invention, the incision is made by a pair of faced clamps, each being in the form of a chute, trough or convex member and each having a sharpened point and sharpened longitudinal edges. In particular, the incision is made in such a way that, when the clamps penetrate the affected organ, two faced semicylindrical cuts are made. In between these cuts the is thus an organ portion which is substantially cylindrical in shape. Immediately following the making of the incision, a tube penetrates. This tube has a point or front end which is sharpened around its circumferential edge and which approximates and moves forward over the clamps until a mutual contact is reached. At that moment, the specimen separates from the remainder of the organ by the combined effects of the cut made by the sharpened edge of the tube and the closing of the clamps. The specimen is then retained by the clamps from where it can be easily retrieved afterwards All the aforementioned stages of operation of the extractor of the present invention can be carried out in rapid sequence, almost totally instanteneously by a physician using only one hand. Moreover, when any of the above-described embodiments is to be used, the extractor of the invention offers the user digital control. In one variation this control is by means of only a latch. More specifically, the device of the present invention has a manual handle or grip which enables the instrument to be operated manually in a digital fashion, by means of latches, knobs, buttons, etc. The specific mode of control used with the handle differs depending on the embodiment. All modes, however, involve sequential operations which can be performed with no interruptions or delays. So short are the time lapses between these operations that the whole procedure can be considered to be just one functional step from beginning to end, with a minimum of patient discomfort and maximum of operator security.

The aforementioned handle of the subject device, preferably similar in configuration to those of pistols, is integrated at least with one straight and long tube located in front of it, the latter tube being enclosed within an external cylindrical jacket located at the tube end opposite the handle. There is at least one lateral opening in this jacket to facilitate the direct observation of the exact site where the specimen is to be taken. In the first of the embodiments, the extractor has two such tubes, both housed in a single cylindrical jacket at the end far from the handle. In the second of the embodiments, there is only one tube coaxial with the jacket.

In both of the embodiments, two rods move inside the respective tube or tubes. One rod for each tube in the first embodiment and two rods in the same tube in the second embodiment. The movement of these rods and their configurations differ depending on the particular embodiment. The end result, however, is similar. In the first embodiment, moreover, an air-suction medium is employed, but not in the second embodiment.

BRIEF DESCRIPTION OF THE DRAWING

The above-described features of the present invention will become clearer upon reading the following detailed description, viewed in conjunction with the accompanying drawing, in which.

DETAILED DESCRIPTION

In the description that follows, the same reference numbers have been used to designate similar parts or structural elements of the embodiments to be described.

Figure 1:
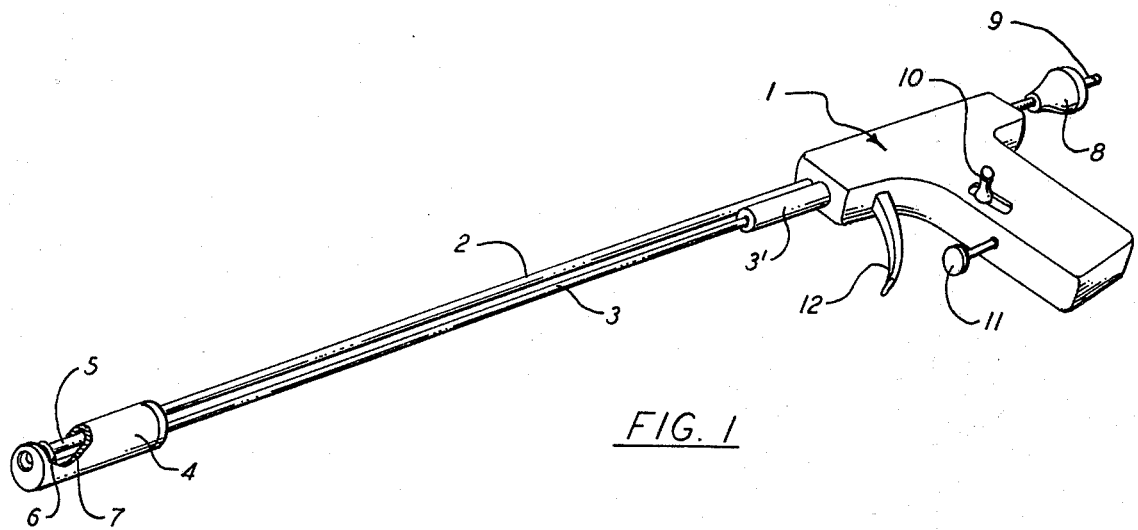
FIG. 1 is a perspective view of a surgical instrument for the extraction of specimens in accordance with a first embodiment of the present invention.
Figure 2:
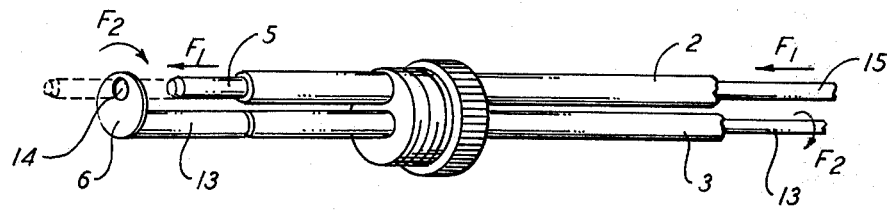
FIG. 2 is an enlarged detail view of the functional end of the instrument of FIG. 1 in which the jacket surrounding such end has been removed.

FIG. 1 shows a first embodiment of a surgical instrument or extractor in accordance with the principles of the present invention. Such instrument comprises a device formed by a handle 1 that in its front supports two straight and parallel tubes 2 and 3. The ends of these tubes opposite the handle are surrounded by a cylindrical jacket 4. As can be seen in FIG. 2, housed inside the jacket 4 are a punch 5, which is rigidly connected to and forms the end of a hollow rod 15 housed inside the upper tube 2, and a rotating guillotine 6, which is solidly connected or affixed to another rod 13 located within the other tube 3. Both elements, the punch 5 and guillotine 6, can be seen through an aperture or lateral window 7 made in the above-mentioned jacket.

The shifting rod 15 housed in the upper straight tube 2 runs along all the handle 1 and protrudes in the back, where is incorporated into a knob or pull 8. It ends then as a tube coupling or as a coupling for something similar 9.

Included in the handle 1 is a shifting button 10 which, as will be explained in more detail below, when operated, frees an internal spring in the handle. This spring operates the running rod 15 with its punch 5, as illustrated by arrow $F_1$ in FIG. 2. The punch then penetrates, let us say, the epithelial tissue of an organ until it is sufficiently introduced in the stroma, since this is the most important part for specimen extraction for biopsies. Another press button 11 included in the handle, can then be operated to retract the punch 5, whereby the specimen defined by the punch is stretched into the form of an elastic cylinder. Finally, operation of a latch 12 also included in the handle, causes the rod 13 to circle about itself within the other tube 3. Such movement of rod 13, in turn, causes the guillotine 6 to cut the specimen defined by punch 5, which specimen has now been stretched from the organ through retraction of rod 15 and, in addition, through suction created at the end 9 of the rod. Once separated from the organ, the specimen can then be taken for histological examination or other examinations.

As can be seen in FIG. 2, which, as above-indicated, shows the active end of the subject device with the jacket 4 removed, the guillotine 6 comprises a disk-shaped element which is solidly connected to the rotating rod 13 and is placed in a manner that allows for free rotation within the tube 3. The disk has an opening 14 aligned with the punch 5. The internal edges of the disk forming such opening 14 are sharpened to permit cutting of the specimen to be extracted. The arrow $F_2$ indicates the rotation of the disk when it is caused to rotate by the latch 12, as a result of the latch being moved as shown by arrow $F_3$ in FIG. 3.

Figure 3:
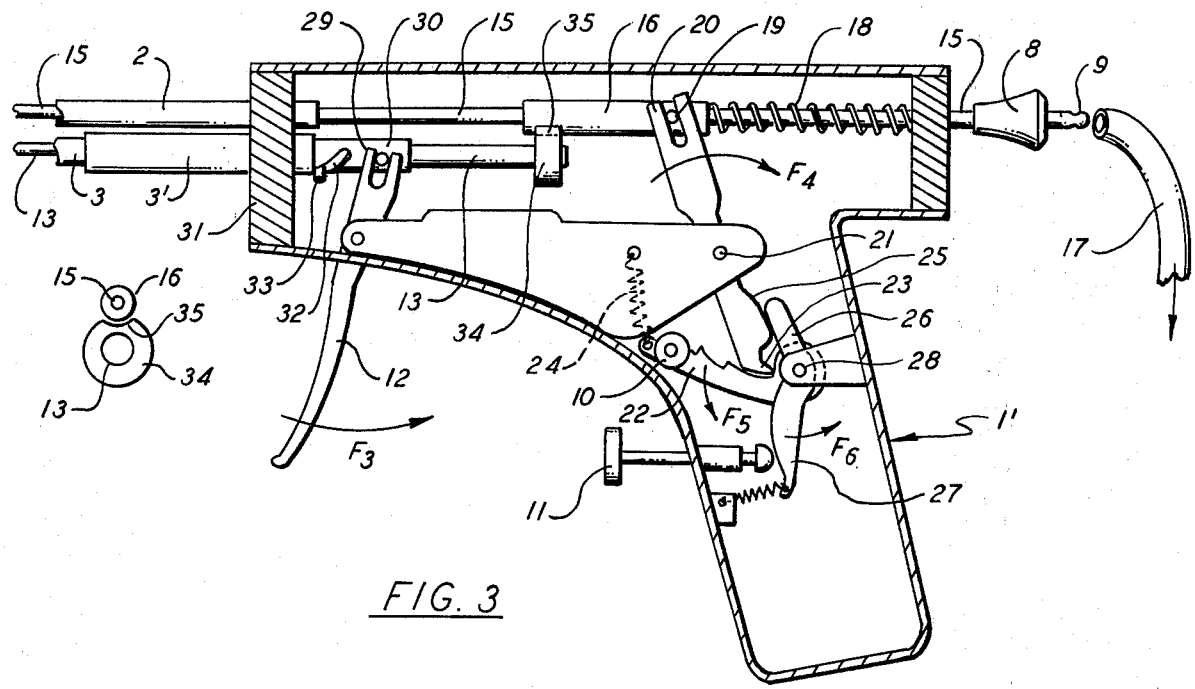
FIG. 3 shows the controlling mechanism for the handle of the instrument of FIG. 1.

As shown in FIG. 3 the handle 1 has a frame 1' similar to that of a pistol handle which is crossed in the upper part by the hollow rod 15 being guided by the upper tube 2. The rod 15 is integrated to a resistant widening 16 and from there extends through the butt of the handle where is joined to a knob or pull 8. It protrudes from knob 8 as a coupling 9 for a rubber tube or something similar 17 for attachment to a vacuum pump, or any other suctioning device not illustratted.

By pressure operated against the widening 16, a helicoidal spring 18 tends to push the rod 15 forward. The widening 16 has, at least, one lateral pivot 19 where a lever 20 hinged at point 21 sets up. When the lever rotates as indicated by arrow $F_4$, due to the manual traction or pull of the knob 8, the lever is retained by a rack 22, the latter preferably having two transitory retention teeth. The rack tends to maintain a meshing position with the end 23 of lever 20 by traction exerted by an open-coil spring 24.

The knob or button 10 is solidly connected to the rack 22. When it is operated as indicated by the arrow $F_5$, it frees the lever 20 so that, by the push of spring 18, the lever rotates counterclockwise to the arrow $F_4$ and, therefore, pushes the punch 5.

There is a face 25 in lower arm of lever 20 to provide support for a finger 26 which is part of another lever 27 hinged to the same fulcrum 28 as the rack 22. Thus, when pressure is exerted against the knob 11, this lever 27 rotates as indicated by the arrow $F_6$, and the finger 26 rotates the lever 20 again in the direction of the arrow $F_4$ to retract the punch 5 being controlled by the spring 18. This retracting action is continued only until the first tooth of the rack is engaged. That is, the rod retraction 15 required at this point is less than that needed at start of operation.

When the punch 5 is retracted by the knob 11, the latch 12 is operated as indicated by arrow $F_3$. Then the forked end 29 of the aforesaid latch 12 moves the tube 30 forward. Within the tube 30 is the rod 13 which is capable of freely rotating, but incapable of axial displacement. The rod 13 forward of the tube 30 is housed, as above-indicated, in the tube 3, the latter tube, in turn, as a supporting measure, being housed in another tube or jacket 3' which is fixed in the frontal wall 31 of handle 1.

The tube 30 has a helicoidal slot 32 therein so that, when axially moved, it rotates the rod 13 by means of a pivot 33 which is located in the slot and solidly connected to the rod. The rotation of rod 13 moves the guillotine 6 to cut the specimen stretched by suction created within the punch 5.

The embodiment of FIG. 1 is also provided with means to assure the physician that no movement that he makes would be outside the correct sequential procedure. In particular, handle 1 is additionally provided with a roller 34 which is solidly connected to the end of rod 13 located in the handle. The roller 34 has a notch 35, the latter notch being visible in the illustration at left side of FIG. 3. When the punch 5 is in a forward position, that is, when the spring 18 reaches its maximum expansion, which is the position illustrated in FIG. 3, the notch impedes the rotation of the rod 13 due to the widening 16 and, therefore, it locks the latch 12.

It is apparent, therefore, that the user cannot operate the latch 12 if the punch is in a forward position. On the other hand, if the knob 11 is operated pulling the punch 5 back into the jacket, the widening 16 is retracted beyond the notch 35, and as a result, the roller 34 can now rotate.

In the same manner, if the latch 12 has been retracted, the roller 34 would have rotated, thereby causing the notch 35 to be out of alignment with the widening 16. In this case, the roller 35 will now stop the spring 18 from moving the tube 15, and, thus, the punch 5 forward, until the latch returns to its inoperative position, thereby causing the guillotine to have its opening 14 again aligned with the tube 5.

As is apparent, in the embodiment of FIG. 1, special attention and care have been used with respect to the particular distribution, location and operating characteristics of the latch and the knobs or buttons 10, 11, 12 including in the handle 1. Such attention has been given so that the movements to be carried out by the user can be done comfortably and easily without adversely affecting the results.

Figure 4:
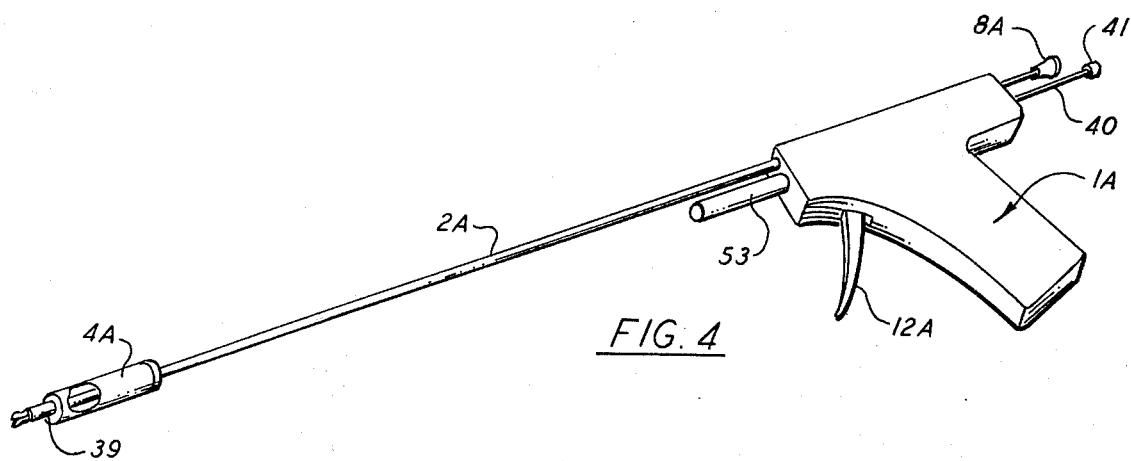
FIG. 4 is a perspective view of a surgical instrument in accordance with a second embodiment of the present invention.

With respect to the second embodiment of the present invention, shown in FIG. 4, it should be pointed out such embodiment represents a simplification (of construction as well as of user's handling) over that of FIG. 1, since it can be operated using a single latch, which has two points of operation in its angular movement.

As can be seen in FIG. 4, this second embodiment of the invention, comprises a handle 1A that in its front supports a single longitudinal hollow tube 2A. The end of the tube 2A opposite handle 1A is surrounded by a cylindrical jacket 4A, the latter jacket being concentric with the tube and having lateral windows 7A.

All operations to be carried out by the device of FIG. 4, that is, the making of a substantially cylindrical incision, extraction of a precise piece defined by this incision, and, finally, cutting this piece to be able to pull it out, are made by operating a latch 12A including in handle 1A, as is explained hereinbelow.

Figure 5:
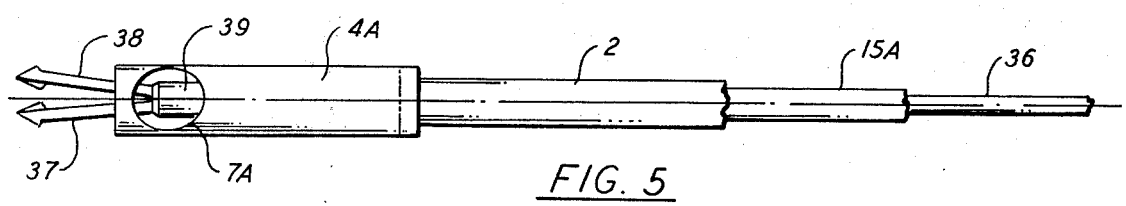
FIG. 5 is an enlarged view of the functional end of the instrument of FIG. 4.
Figure 6:
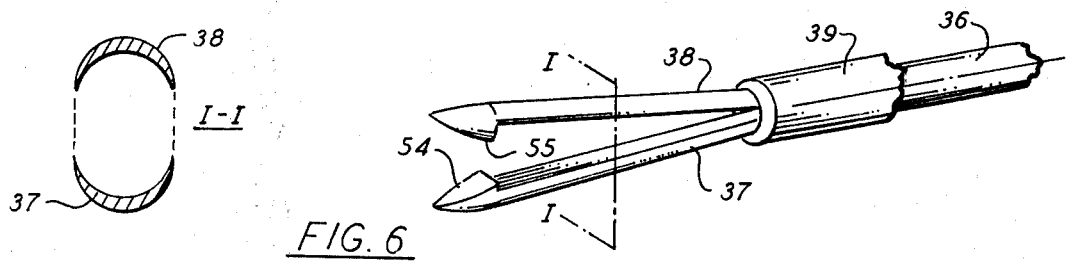
FIG. 6 shows an enlarged detailed view and a cross section thereof of the functional end shown in FIG. 6 in which the jacket surrounding such end has been removed.
Figure 7:
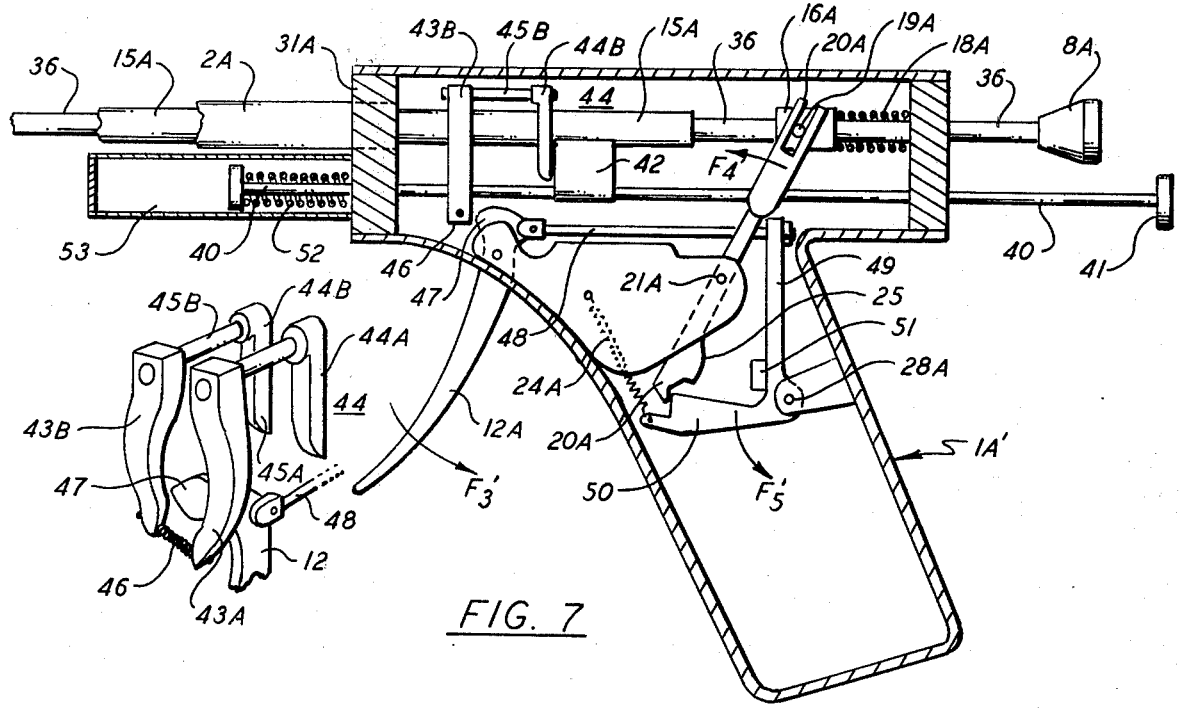
FIG. 7 shows the control mechanism of the handle of the instrument of FIG. 4.

More specifically, as shown in FIG. 5, two concentric rods 15A and 36 are included within the tube 2A, both being able to slide in a coaxial direction. The first rod 15A is hollow so that the second can move within it, as indicated in FIGS. 5 and 7. The rod 15A ends at its active extreme as a punch with sharpened edges 39, while the internal rod 36 ends at its active extreme as two-faced members. In particular, as can be seen from FIGS. 5 and 6, the aforesaid two members are in the form of a pair of elastically separated grips or clamps 37 and 38, each of which has the shape of a convex member, chute, or trough with sharpened edges. When the punch 39 moves forward, these grips unite and, by means of the sharpened front portion or knives 54 and 55, cut the piece of organ to be examined. Moreover, both grips end in very sharp points so as to be able to make an incision when impulsed by the rod 36 into the affected organ. This movement of the rod 36, in turn, results from the action of a helicoidal extension spring 18A housed in frame 1A of the handle 1A. Before this process, a knob 8A, located at the end of rod 36 which extends from the butt of the handle, is pulled and the cube 16A, the pivot 19A and the lever 20A, included in the handle 1A as shown in FIG. 7, press the spring 18A. The lever 20A pivots on the fulcrum 21A moving counterwise of the arrow $F'_4$, and it locks in its lower end due to the effect of spring 24A which tractions or holds the bar 50 pivoting on the fulcrum 28A. The later bar, in turn, is solidly connected to a lever 49 which is connected to a rod 48 pulled by the latch 12A. When the latch 12A is thus operated in the arrow direction $F'_3$, the rod 48 rotates the unit 49–50 in the direction of the arrow $F'_5$, stretching the spring 24A to free the lever 20A. The spring 18A then pushes the bar 36 in a forceful manner, so that the grips 37–38 penetrate the affected organ and produce the mentioned incision.

On the other hand, the rod 15A, whose end forms the punch 39, is freely moving relative to the rod 36. The rod 15A is, however, soldered to a cylinder 42 housed in handle 1A. The latter cylinder, in turn, is solidly connected to a straight rod 40 which extends through the handle and is connected opposite the butt end thereof to a knob 41. The other end of the rod 40 passing out the frontal wall 31A of handle 1A, is joined to a disc that presses an expansion spring 52, housed in a jacket-tube 53 affixed to the handle front wall.

While the spring 52 tends to move the rod 40 forward, such action is impeded by the two parallel branch retainer 44 included in the handle. As can be seen in the perspective detail at the side of FIG. 7, retainer 44 includes two substantially parallel, short resistent bars, 44A and 44B which are joined to respective curved levers 43A and 43B via rods 45A and 45B, respectively. The levers 43A and 43B are acted upon, one to the other, by a spring 46 or by elastic plates (not illustrated) or other similar pushing apparatus. As can be appreciated, the two curved levers 43A and 43B have a tendency, due to the action of spring 46, of staying approximate one another. However, when the conic point 47 which is solidly connected to the latch 12 moves forward, it penetrates between the levers or curved branches 43A and 43B and separates them, thereby rotating in opposite directions the bars 44A and 44B. This action separates the bars 44A and 44B enough so that the rod 15A is pushed forward by the pull of spring 52, which spring acts on rod 15A via rod 40 and cylinder 42.

Consequently, starting by pulling the knobs 8A and 41, the two springs 18A and 52 are compressed and with enough power to push their respective rods. When the latch 12A is operated as indicated by arrow $F'_3$, first the lever 20A is liberated from its lower retainer. As a result, the bar 36 is quickly pushed until the grips 37–38 have sufficiently penetrated into the organ to be analyzed. Continuing the latch operation in the direction of the arrow $F'_3$, the point 47 will then open the retainer 44 and will loosen the rod 40. By means of the cylinder 42, the latter rod will move the tube 15A with its punch 39 to the bottom of the incision previously made, thereby causing the organ to be cut by means of the knives 54-55 which close when the punch 39 advances. Afterwards, the user can remove the instrument from the patient holding within its convex grips 37, 38 the extracted specimen.

As can be appreciated from the aforesaid, therefore, this second embodiment of the device, while differing in detail with respect to the first embodiment, performs the desired extraction process in accordance with the same basic concept. It, however, has the advantage that it is more easy to operate, it provides greater visibility, and there is no need to connect it to a suctioning device.

When manufacturing the surgical instrument that has been just described and illustrated, modifications and/or imrovements can be added. These should all be considered as other embodiments constructed within the scope of protection of the present invention, such scope being determined by the following appended claims.

What is claimed is:

1. A surgical instrument for performing biopsies of an organ comprising:
   a housing;
   a first cutting means supported by said housing for penetrating and cutting said organ;
   a first releasing means for releasing a latching means;
   a first latching means responsive to said first releasing means for rapidly moving said first cutting means over a short distance when released;
   a second cutting means supported by said housing for totally releasing the portion of said organ cut by said first cutting means;
   a second releasing means for releasing a latching means;
   a second latching means responsive to said second releasing means for rapidly moving said second cutting means over a short distance when released;
   and control means for sequentially operating said first and second releasing means.

2. A surgical instrument in accordance with claim 1 in which said first cutting means includes:
   a tube fixed to said housing;
   an axle slidably mounted within said tube and operatively attached to said first latching means;
   and a punch arranged at the end of said axle.

3. A surgical instrument in accordance with claim 2 in which said second cuttng means includes;
   another tube fixed to said housing;
   another axle slidably, axially and rotatably mounted within said other tube and having a free end attached to said second latching means, whereby said other axle can be rotated rapidly;
   a disc mounted at the other end of said other axle and having a perforation which is aligned with said punch and which has sharpened edges, said perforation upon the rotation of said other axle moving across said punch and cutting said portion of said organ lodged thereon after operation of said punch.

4. A surgical instrument in acordance with claim 2 in which said axle is hollow and its end opposite the end attached to said punch extends beyond said first latching means and includes a connecting means adapted to be connected to a vacuum source.

5. A surgical instrument in accordance with claim 1 in which said first cutting means comprises:
   an axle having an end attached to said first latching means;
   first and second convex cutting members which face one another and have an elastic tendency to separate from one another, said cutting members having end portions attached to the opposite end of said axle and having opposite end portions with sharpened cutting edges which in an inner portion have confronted cutting edges finished in convex cavities of said convex cutting members.

6. A surgical instrument in accordance with claim 5 in which:
   said second cutting means includes a hollow punch having an end attached to said second latching means and having an inner diameter which is less than the distance separating said opposite end portions of said convex cutting members;
   and said axle and convex cutting members are mounted so as to be slidable within said punch.

7. A surgical instrument in accordance with claim 6 in which the displacement run of said axle is determined by said first latching means.

8. A surgical instrument in accordance with claim 6 which further includes:
   a tube secured to said housing and within which said axle, cutting members and punch are displaceably mounted;
   an adjustable sleeve having at least one lateral window and supported at the free end of said tube which coincides with said convex cutting members, said sleeve extending slightly beyond the end of the convex cutting members when they are in a retracted position and serving as a bearing means on the organ to be cut and as a limit to the displacement of said convex cutting members.

* * * * *